United States Patent
Griffin et al.

(10) Patent No.: US 6,932,769 B2
(45) Date of Patent: Aug. 23, 2005

(54) ULTRASONIC OCCUPANT DETECTION AND CLASSIFICATION SYSTEM

(75) Inventors: Dennis P. Griffin, Noblesville, IN (US); William W. Fultz, Carmel, IN (US)

(73) Assignee: Delphi Technologies, Inc., Troy, MI (US)

(*) Notice: Subject to any disclaimer, the term of this patent is extended or adjusted under 35 U.S.C. 154(b) by 127 days.

(21) Appl. No.: 10/447,306

(22) Filed: May 28, 2003

(65) Prior Publication Data

US 2004/0242997 A1 Dec. 2, 2004

(51) Int. Cl.[7] .................................................. A61B 8/00
(52) U.S. Cl. ........................................ 600/437; 701/47
(58) Field of Search .................. 600/407–472; 367/7, 11, 130, 138; 73/588, 618–641; 701/45–47; 128/916; 280/734, 735; 180/271

(56) References Cited

U.S. PATENT DOCUMENTS

| | | | | |
|---|---|---|---|---|
| 5,890,085 A | * | 3/1999 | Corrado et al. | 701/47 |
| 6,324,453 B1 | * | 11/2001 | Breed et al. | 701/45 |
| 6,571,018 B1 | * | 5/2003 | Kim | 382/245 |
| 6,585,647 B1 | * | 7/2003 | Winder | 600/437 |

* cited by examiner

Primary Examiner—Ali Imam
(74) Attorney, Agent, or Firm—Stefan V. Chmielewski

(57) ABSTRACT

An ultrasonic occupant detection and classification system transmits an ultrasonic signal and receives a composite signal containing interference created between the transmitted ultrasonic signal and a reflection of that signal from a moving occupant. A signal component of the received, composite signal is extracted by amplitude demodulation and bandpass filtered to derive a frequency characteristic that is compared to stored frequency data; and the derived and stored data are compared to identify frequencies characteristic of respiration and/or other movements characteristic of living beings.

20 Claims, 10 Drawing Sheets

| TABLE 1 (3-300 Hz) ||
|---|---|
| CENTER FREQUENCY (Hz) | BANDWIDTH (Hz) |
| 4 | 2 |
| 7.5 | 5 |
| 15 | 10 |
| 25 | 10 |
| 35 | 10 |
| 50 | 20 |
| 70 | 20 |
| 90 | 20 |
| 150 | 100 |
| 250 | 100 |

FIG. 9

ULTRASONIC OCCUPANT DETECTION AND CLASSIFICATION SYSTEM

TECHNICAL FIELD

The technical field of this invention is occupant detection and classification.

BACKGROUND OF THE INVENTION

The detection and classification of a live being, human or other, has a variety of useful applications in the field of security (intruder detection), safety (trapped occupant detection) and personal health and medical applications. A variety of systems have been described, developed or even provided for such purposes, for building rooms, vehicles and other defined volumes. A technology used in many of these systems is ultrasound: that is, acoustic wave signals at frequencies above the normal range of human hearing. Prior art systems are described that transmit ultrasonic signals in a pulse mode and analyze returning, reflected signals using a "time of flight concept;" while other such systems employ continuous transmission and analyze the returning, reflected signals for Doppler shift. Many of the systems are successful in certain applications and within certain limits, in detecting a moving occupant and generating an alert that is to be interpreted as a detection of a living occupant. But the systems are hampered by their inability to deal with problems in acoustic impedance of transmission media and reflecting occupants and wave interference in the received signals between transmitted and reflected acoustic waves. They generally tend to be limited to the detection of gross body movements, and are not sufficiently sensitive to reliably detect the small movements characteristic of respiration that involve only very small body movements.

SUMMARY OF THE INVENTION

The ultrasonic occupant detection and classification system of this invention overcomes many limitations of the prior art systems and successfully detects and classifies living occupants of a volume through detection of movements due to respiration. Unlike ultrasonic occupant detection systems of the prior art, the system of this invention is designed to derive information from interference created between a transmitted ultrasonic signal and a reflection of that signal from a moving occupant. This information is present as an amplitude modulation on the received reflection of the transmitted signal, when an occupant is moving within the transmission/reception volume in a fore and aft direction with reference to the direction of transmitted and reflected ultrasonic signals. The system is sufficiently sensitive that it is often capable of detecting respiratory chest movements beneath clothing.

The invention is a method and apparatus for classifying an occupant in a predetermined volume in which an ultrasonic signal having a predetermined transmitter amplitude and a predetermined ultrasonic frequency is transmitted through the predetermined volume. A composite ultrasonic signal is received that has a signal component produced by interference between the transmitted ultrasonic signal and a returning reflection of the transmitted ultrasonic signal from an occupant within the predetermined volume. The composite ultrasonic signal is amplitude demodulated to isolate the signal component, which is analyzed to derive frequency data. Finally, the occupant is classified within the predetermined volume from the derived frequency data of the interference signal component.

The analysis is preferably performed in the frequency domain by storing frequency data characteristic of a live occupant movement, comparing the derived frequency data with the stored frequency data, and classifying the occupant as a living being if the derived frequency data and the stored frequency data match within predetermined criteria. In a preferred embodiment, the signal component is bandpass filtered in a parallel manner to extract present amplitude and other information in one or more frequency bins within a frequency range characteristic of respiration; and the comparison with stored data for the frequency bins will reveal the presence of respiration, to classify the occupant as a living being, and potentially the rate, and/or rate of change, of respiration, which can potentially provide further classification, depending on expectations regarding the predetermined volume and its likely occupants. The applications of the invention include the sensing of living beings and the monitoring of life functions such as respiration and other body movements having characteristic frequencies for trapped occupant sensing, intruder sensing, health and activity monitoring and similar functions.

BRIEF DESCRIPTION OF THE DRAWINGS

The present invention will now be described, by way of example, with reference to the accompanying drawings, in which:

FIG. 9 is a table useful in describing a portion of the operation of the invention.

DESCRIPTION OF THE PREFERRED EMBODIMENT

Figure 1:
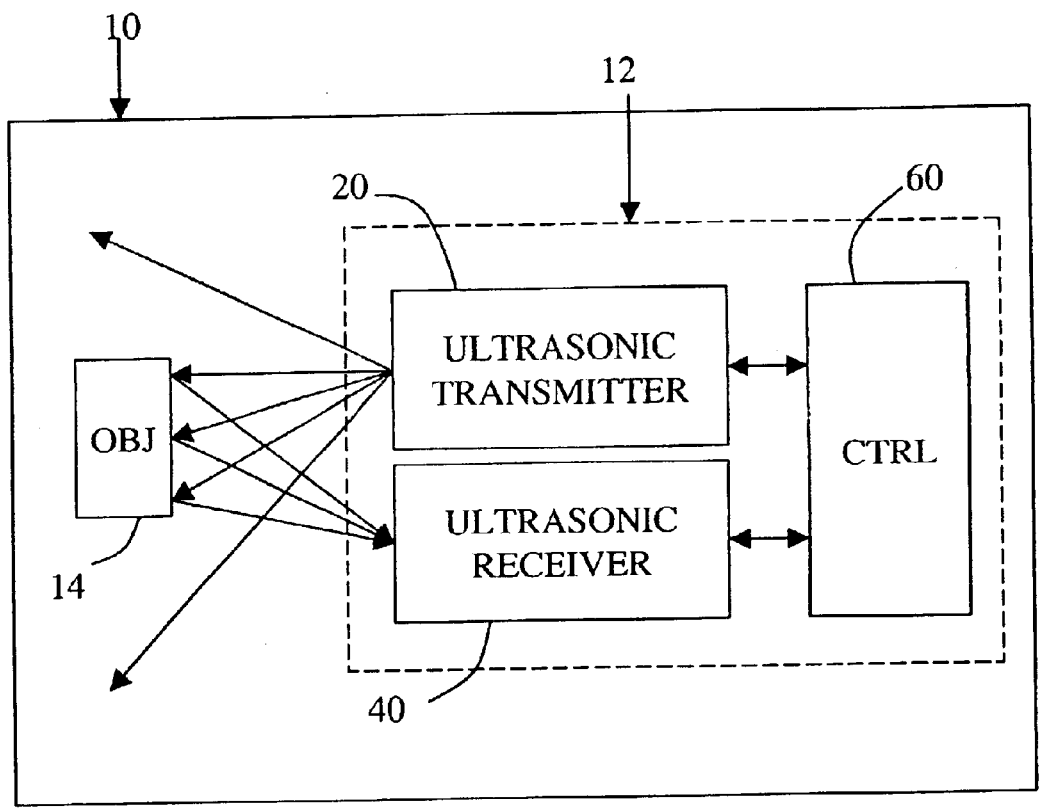
FIG. 1 is a block diagram of an ultrasonic occupant detection system according to the invention.

The ultrasonic occupant classification system described in this document incorporates a sensor using an ultrasonic transmitter and receiver to achieve a high level of motion sensitivity. This sensor design operates in a near continuous mode and capitalizes on the properties of acoustic impedance and acoustic interference (which can be problems areas in other sensor designs) to perform the occupant sensing function. In a typical application, the sensor would be mounted strategically to allow the transmitter to emit ultrasonic signals into a target volume. In the case of a vehicle interior application, for example, a beam angle of 40 to 50 degrees allows a broad area of coverage without degradation of the sensitivity of the sensor. The reflected signals from the target are detected by the ultrasonic receiver and passed through a signal processing circuit that detects changes in the signals that result from movement and/or dynamic changes in the target field of view. Even with a relatively low frequency 40 kilohertz ultrasonic signal, the wavelength (based on the average speed of sound through air) is approximately 8.5 millimeters; and relatively small movements of the target result in phase changes in the reflected signals. These phase changes in the target's ultrasonic reflections combine to create frequency, amplitude and phase changes in the composite reflected signals at the receiver. The sensor detects these changes and is capable of detecting even slight movements such as respiration and other movements of a living being. In addition, movement detection behind low acoustic impedance materials, such as blankets or clothing, is possible with this sensor.

Acoustic impedance, Z, is defined as: Z=pv, wherein p indicates material density and v indicates acoustic velocity. The reflectivity R of the target can be determined by:

$$R=(Z_2-Z_1)^2/(Z_1+Z_2)$$

The transmission coefficient of the target can be determined by:

$$T=4*Z_1*Z_2/(Z_1+Z_2)^2$$

wherein $Z_1$ is the propagation medium impedance and $Z_2$ is the target impedance. These equations show that the transmission coefficient is equal to 1 and reflection is zero if $Z_1$ is equal to $Z_2$; and the reflection increases (and transmission decreases) with increasing difference between $Z_1$ and $Z_2$. Thus, ultrasonic energy is reflected by targets primarily because of a discontinuity in the acoustic impedance at the boundaries of different materials. Since the acoustic impedance of air is low relative to most targets, the typical impedance mismatch for an air-born ultrasonic wave encountering a non-gaseous material is several orders of magnitude (for example, $Z_{water}/Z_{air}=~4000$). As a result, the sensor needs to have considerably high sensitivity in order to extract both slight primary target movement and also the weak reflections from secondary target movement.

Probably the best way to describe the use of acoustic interference by the sensor of this invention is to first describe a scenario where there is a minimum reflected signal. In this case, the sensor transmits a signal that propagates through air reaching a target whose round trip distance from the sensor is equal to an odd number of half wavelength multiples of the transmitted frequency. As a result of the target distance, the reflected signal from the target is 180 degrees out of phase with respect to the transmitted signal, and the resulting interference between the continuously transmitted signal and the reflected signal from the target would result in a minimum amplitude composite signal at the receiver.

If on the other hand, the target was at a round trip distance equal to a multiple of the wavelength of the transmitted frequency, the reflected signal from the target would be in phase with respect to the transmitted signal, and the resulting interference would result in a maximum amplitude composite signal at the receiver.

Any other target distance will create a signal that is between the minimum and maximum levels. Further, any motion of the target will essentially create a modulated reflected signal, with the operating "carrier" frequency of the reflected signal equal to the frequency of the transmitted signal, and the "modulation" of the amplitude of the carrier being the result of the target movement and distance from the sensor. The apparatus of this invention is specifically designed to detect the frequency components of target movement, although it can also measure target distance. It should also be noted that the sensor is able to detect concurrent multiple target movements (frequencies).

FIG. 1 shows an ultrasonic occupant detection system 12 for use in a detection environment or volume 10. Examples of such an environment include a passenger compartment or storage area of a motor vehicle, a room of a building. Alternatively, the environment could be the volume above a bed, an area outside a building or almost any other volume in which ultrasonic detection is desired. System 12 has an ultrasonic transmitter 20 and an ultrasonic receiver 40, together with a control 60, and is arranged so that transmitted ultrasonic signals at a predetermined ultrasonic frequency from transmitter 20 directed at an object or occupant 14 will be at least partially reflected by the object or occupant; and the reflected signals from occupant 14 will interfere with the transmitted (pre-reflected) signals to create a composite signal in volume 10. The composite signal comprises a carrier signal at the ultrasonic frequency that is amplitude modulated by an interference generated signal component at a much lower frequency; and this composite signal is received by ultrasonic receiver 40. The received ultrasonic signal is demodulated in receiver 40 to separate the signal component, which is analyzed by control (CTRL) apparatus 60 to determine the frequency content thereof and classify the occupant according to predetermined criteria.

The interference in the ultrasonic signals before and after reflection is generated by movement of occupant 14 toward or away from the transmitter, which movement creates phase changes in the ultrasonic signals as the distance between the transmission point of the signals in transmitter 20 and the reflecting surface of occupant 14 varies in the direction of signal transmission between even and odd numbers of half wavelengths of the predetermined frequency so as to create reinforcement peaks and cancellation troughs in the interference signals. The phase changes manifest themselves as the signal component, which has a frequency content of these interference signals corresponding to the frequency of the motion. This frequency content is extracted from the signal component by demodulation and filtering to derive frequency data that is analyzed in control 60 to classify the occupant according to predetermined criteria involving stored frequency data characteristic of live occupant movement. With the proper choice of the predetermined frequency, even very small movements such as respiration of a living person or animal can be easily detected, as explained below.

Figure 2:
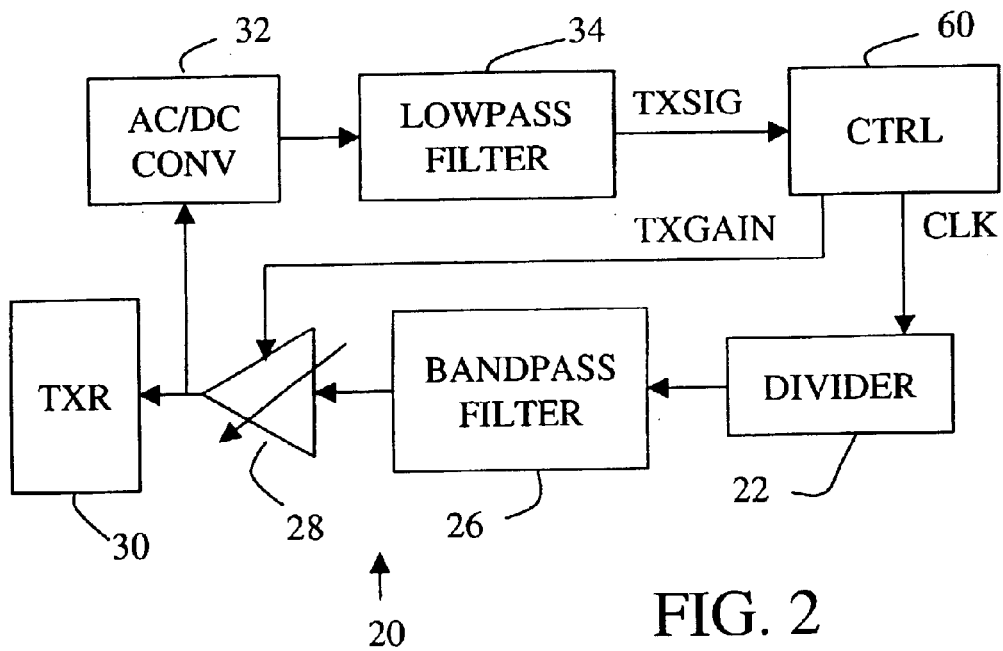
FIG. 2 is a block diagram of an ultrasonic transmitter for use in the apparatus of FIG. 1.

FIG. 2 shows ultrasonic transmitter 20, which generates or derives an oscillator signal in a known manner: in this embodiment from a switching (square wave) signal CLK output by control 60. Divider 22 divides signal CLK as required to obtain a desired predetermined frequency; and the output of divider 22 is processed in a bandpass filter (or filters) 26 to suppress harmonics and leave only an essentially sine wave signal at the desired, predetermined frequency (typically the fundamental frequency of the rectangular wave). The resulting sine wave is amplified in a variable gain amplifier 28, with gain controlled by signal TXGAIN from control 60, and passed to an ultrasonic transmitting transducer (TXR) 30 to generate a transmitted ultrasonic wave at the predetermined frequency moving toward occupant 14. The output of amplifier 28 is also converted to a DC value in (AC/DC CONV) 32 and low pass filter 34, the output TXSIG of which is provided to control apparatus 60 for sensor self diagnostic purposes. Thus, the transmitted ultrasonic signals have the predetermined frequency (typically selected to match the particular transducers used: e.g. 40 kilohertz) and a predetermined, controlled amplitude.

Figure 3:
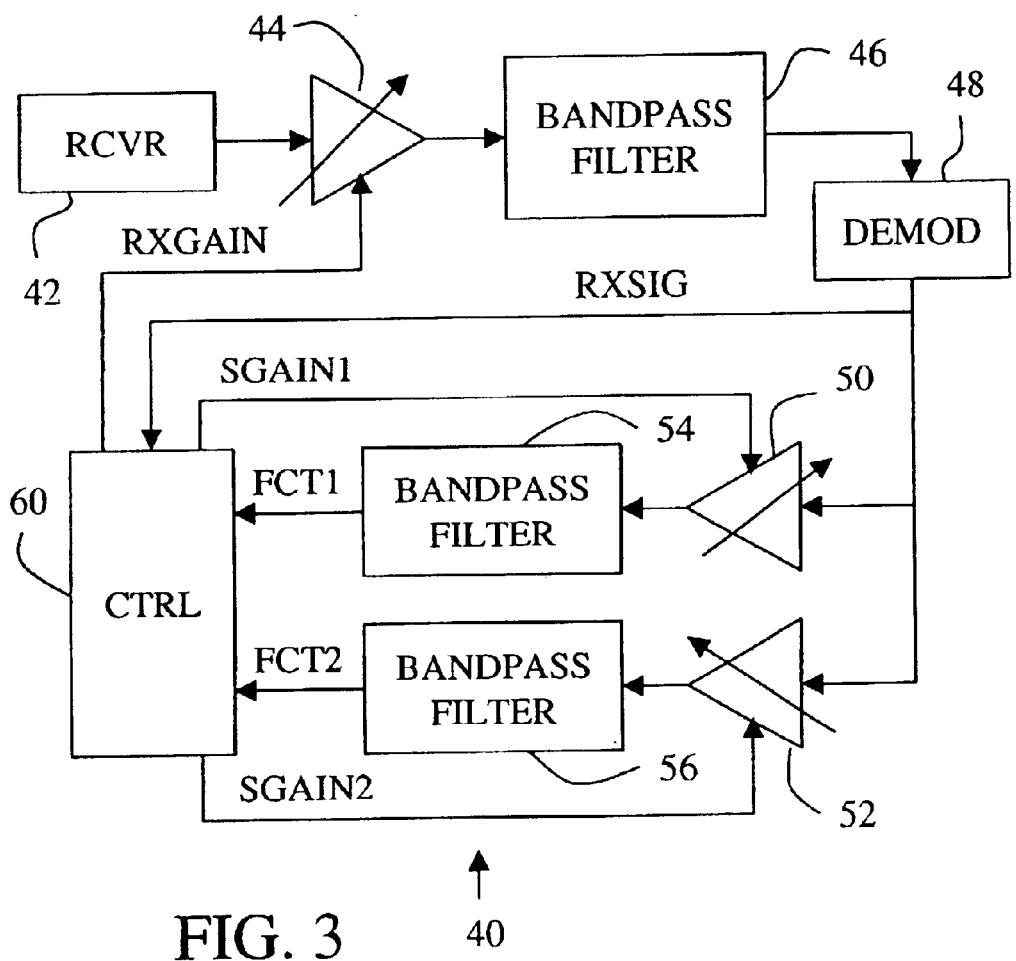
FIG. 3 is a block diagram of an ultrasonic receiver for use in the apparatus of FIG. 1.

FIG. 3 shows ultrasonic receiver 40, which receives a composite signal at the ultrasonic signal due to a reflection of the transmitted ultrasonic signal from an occupant. Ultrasonic receiving transducer (RCVR) 42 provides an output to a variable gain amplifier 44, which amplifies the received composite signal and provides it to a bandpass filter 46 tuned to pass the predetermined ultrasonic frequency. Due to reflection by a moving occupant 14 and interference between the pre-reflected transmitted signal and the post-reflected transmitted signal, the signal from filter 46 may contain an amplitude modulation on the predetermined frequency sine wave (which is now a carrier signal). The amplified and filtered signal from filter 46 is detected in a demodulator (DEMOD) 48, which is an AM demodulator (envelope detector) as known in the art. The output of demodulator 48 is provided as signal RXSIG to control apparatus 60, which determines therefrom a gain control signal RXGAIN that is output to control the gain of amplifier 44. Signal RXSIG from demodulator 48 is also separately provided to each of two gain controlled amplifiers 50 and 52. The output of amplifier 50 is provided to a bandpass filter 54, the output signal FCT1 of which is provided to control apparatus 60. Likewise, the output of amplifier 52 is provided to a bandpass filter 56, the output signal FCT2 of which is also provided to control apparatus 60. Bandpass filters 54 and 56 provide preliminary separation of the demodulated signal into passbands most likely to include frequency content of functions of a living being: for example, 0.3–3 Hertz (filter 54) for respiration and 3–300 Hertz (filter 56) for general body movement and other movements within the range of the sensor, with additional, more particular analysis to be performed within control apparatus 60. Clearly, any convenient number of such bandpass filters may be used. Control apparatus 60 generates gain control signals SGAIN1 and SGAIN2 provided to control the gains of amplifiers 50 and 52, respectively.

Figure 4:
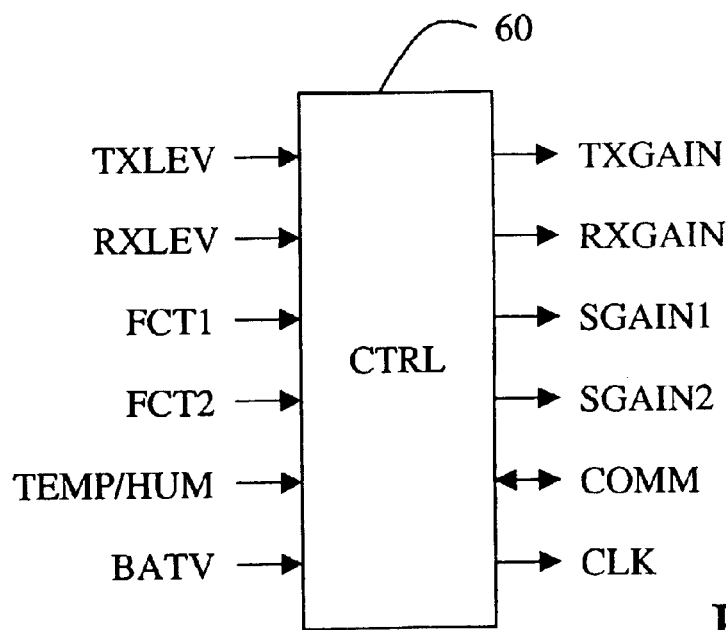
FIG. 4 is a block diagram of a control for use in the apparatus of FIG. 1 showing selected inputs and outputs.

Control apparatus (CTRL) 60 is shown in FIG. 4 with selected inputs and outputs used or potentially used in this invention. The inputs include TXSIG from low pass filter 34, RXSIG from detector 47, FCT1 from bandpass filter 54, FCT2 from bandpass filter 56, BATV from a battery or other DC power supply and, optionally, TEMP/HUM from temperature and/or humidity sensors, in a trapped occupant sensing application. Outputs include TXGAIN, RXGAIN, SGAIN1 and SGAIN2 to amplifiers 28, 44, 50, and 52, respectively, and CLK to divider 22. COMM is a connection to a bidirectional, preferably digital, communication bus. Control apparatus 60 preferably comprises a digital computer with a stored operating program, and further includes such electronic power and signal conditioning apparatus as analog/digital converters, filters, etc. as would be considered necessary and/or beneficial by those skilled in the art.

Figure 5:
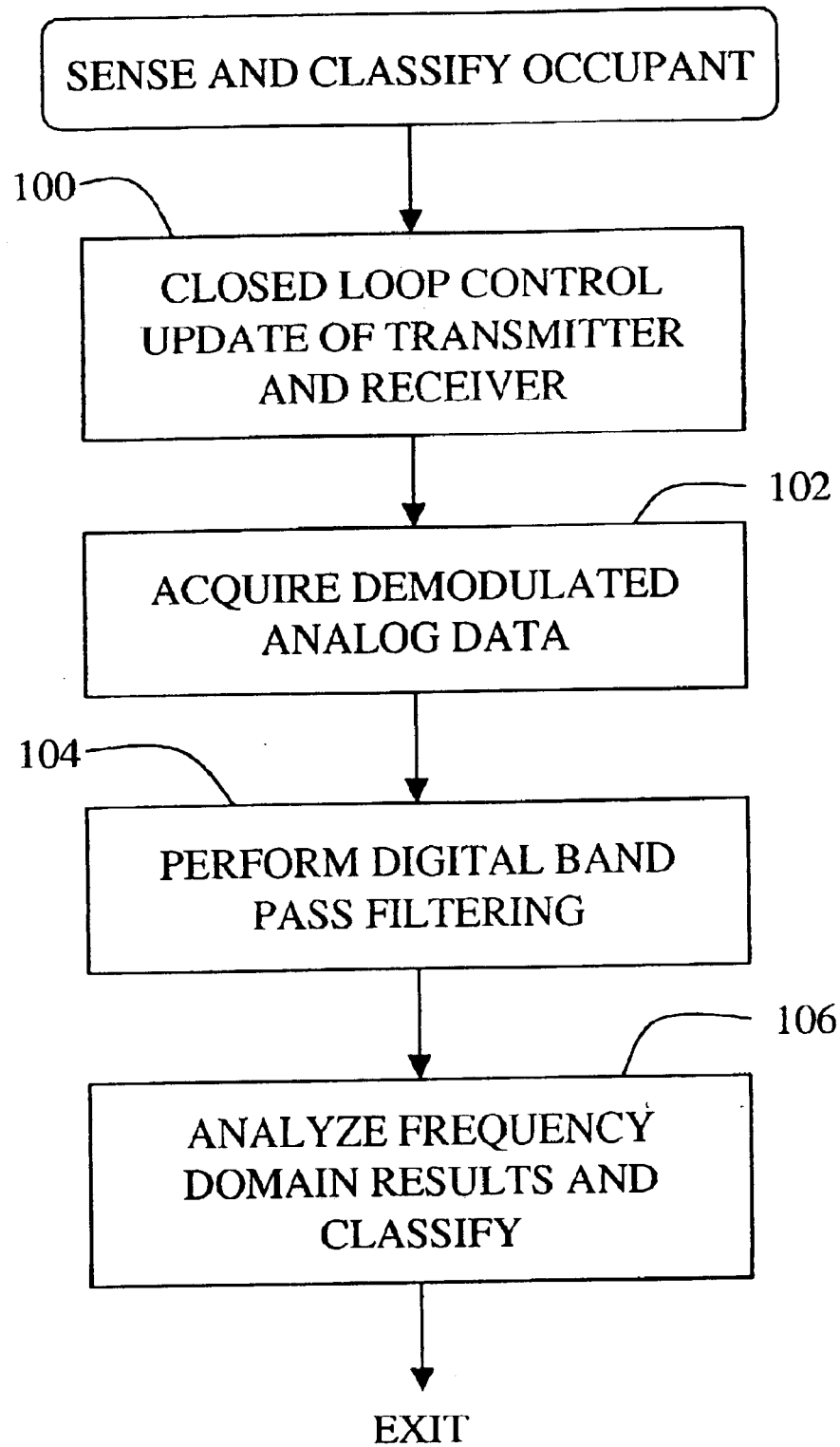
FIGS. 5, 6, 7A–7B, and 8A–8C show flow charts useful in describing the operation of the invention.

The operation of this invention is described as controlled by the program stored in control apparatus 60, with reference to several flow charts. The main program, SENSE AND CLASSIFY OCCUPANT, is shown in the flow chart of FIG. 5. It begins at step 100 by updating closed loop control of the transmitter and receiver. Briefly, the amplitude of the transmitted signal is controlled by a gain control signal TXGAIN based on the available power source DC voltage level BATV; and the amplitude of the receiver is controlled by a signal RXGAIN in an automatic gain control loop based on the demodulated receiver signal RXSIG. In addition, the transmitter gain TXGAIN may optionally be reduced if the receiver gain RXGAIN abuts a minimum limit value, so that the receiver automatic gain loop may function properly. The transmitter gain control will be described in greater detail in connection with the flow chart of FIG. 6; and the receiver gain control will be described in greater detail in connection with the flow chart of FIG. 7A-7B.

At step 102, the analog data of signals TXSIG, RXSIG, FCT1 and FCT2 is updated. Part of this process is the analog/digital conversion process, with the stored, updated data being in digital form for processing in the program.

Additional, digital, bandpass filtering is performed at step 104 on the input signals FCT1 and FCT2. Signal FCT1, which has already been filtered to a passband of 0.1 to 3.0 Hertz, is further subdivided into a plurality of frequency bins covering frequency sub-ranges of the full passband: for example, 15 frequency sub-ranges of 0.2 Hertz bandwidth each (that is, 01.–0.3 Hertz, 0.3–0.5 Hertz, etc). Signal FCT2 is similarly further subdivided into a plurality of frequency bins covering frequency sub-ranges of the full passband: for example 10 frequency sub-ranges as shown in TABLE 1, which is shown in FIG. 10. This further division of the signals into frequency bins covering frequency sub-ranges generates data for developing a frequency characteristic for each signal. The actual filtering is preferably performed by a bandpass filter calculation subroutine called, for each new value of FCT1 or FCT2, in a loop applying the filter subroutine for each of the frequency bins associated with that variable. The bandpass filter subroutine used in this design is a fixed-point implementation of a digital recursive type of filter also known as an IIR (Infinite Impulse Response) filter in the form of:

$$Y_N = X_0 A_0 + X_{N-1} A_1 + X_{N-2} A_2 + Y_{N-1} B_1 + Y_{N-2} B_2$$

In the equation, $X_0$, $X_{N-1}$, $X_{N-2}$ are the present, previous and twice previous input values, $Y_N$, $Y_{N-1}$ are the previous and twice previous output values, $Y_N$ is the new output value, and $A_0$, $A_1$, $A_2$, $B_1$, $B_2$ are constants. This type of digital filter is known by those skilled in the art. For the example described above, a new value of FCT1 would call the bandpass filter subroutine to apply the programmed calculation repeatedly for each of frequency bins F=1–15 in a loop, with each application using the new value of FTC1 (as well as the two previous values of the new data) and the two retained previous filtered values of $FTC1_F$ to produce a new filtered value of $FTC1_F$. The same would be done for each of frequency bins G=1–10 in a loop with each new value of $FTC2_G$. The specific filter coefficients for each of the frequency bins are passed to the bandpass filter calculation routine as input arguments. Those skilled in the art would recognize that the results of the bandpass filtering are rectified and low pass filtered as a part of the signal processing done in the CONTROL program to provide the "frequency bin" data. The low pass filter used in this design is also a digital recursive filter know by those skilled in the art, in the form of:

$$Y_N = X_0 A_0 + Y_{N-1} B_1$$

At step 106, the data derived in step 104 is analyzed, with reference to stored data indicating frequency compositions characteristic of specific movements, particularly those characteristic of a live being, such as respiration or body movements, and any movements detected in this process are classified as to the characteristic movement indicated. Appropriate flags are set indicating if any respiration or other live occupant movements are identified and appropriate indicators or warnings are actuated. Further details of this analysis and classification process are described in the flow chart of FIG. 8A-8C.

Figure 6:
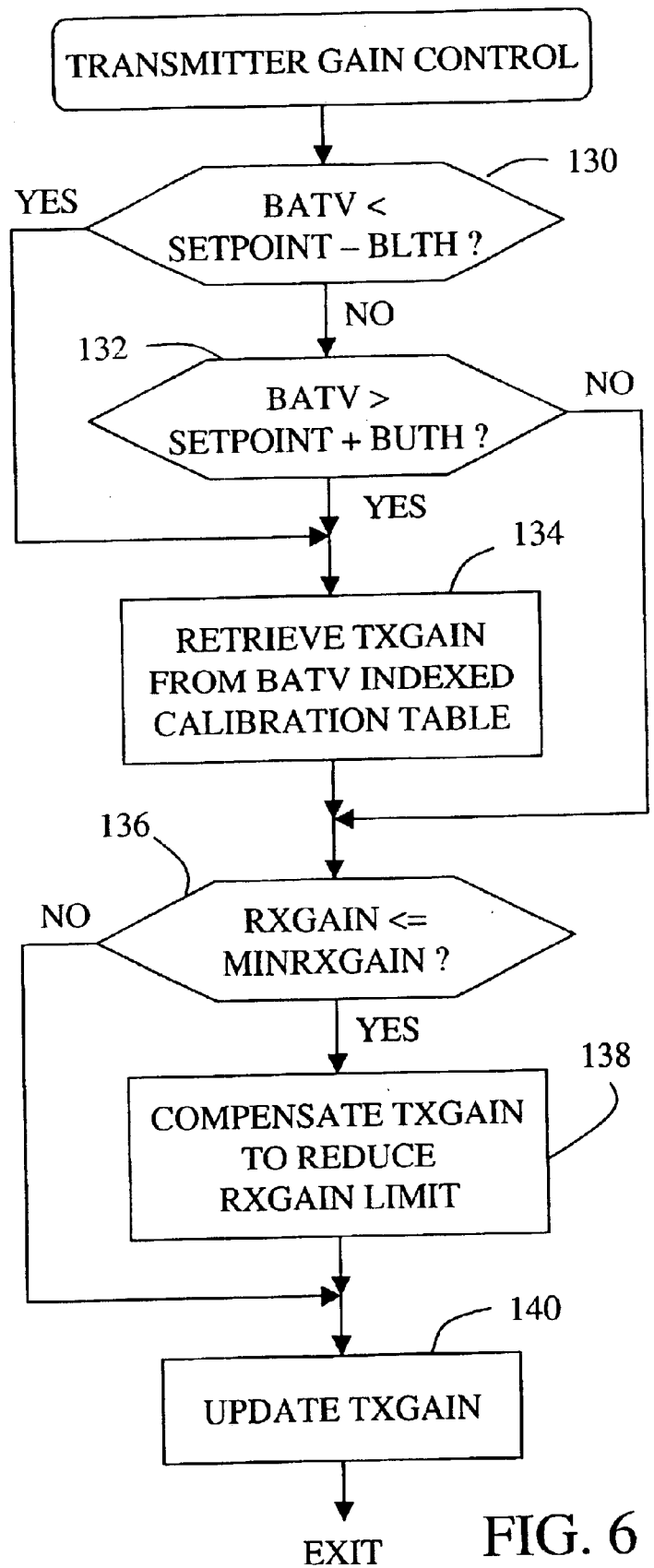

FIG. 6 shows a flow chart for the routine TRANSMITTER GAIN CONTROL Beginning at step 130, the routine determines if the power source DC voltage level BATV is less than a nominal SETPOINT (that was established during initialisation of the CONTROL) minus a lower threshold LTH. If the answer is yes, the routine proceeds to step 134 and retrieves a value TXGAIN from a lookup table using BATV as the input value and establishes a new SETPOINT.

If the answer is no, the routine determines, at step 132, if the power source DC voltage level BATV is greater than the nominal SETPOINT plus an upper threshold UTH. If the answer is yes, the routine likewise derives TXGAIN from the BATV indexed calibration lookup table at step 134 and establishes a new SETPOINT in accordance with the new value of BATV. If the answer is no, or from step 134 in any case, the routine proceeds to step 136 and determines if the value of the receiver gain RXGAIN is less than or equal to a calibrated minimum value MINRXGAIN. If the answer is yes, the routine determines at step 138 a compensation to the transmitter gain TXGAIN to reduce the RXGAIN limit, so that RXGAIN may be increased in its own gain control routine. At step 140, the routine outputs an updated value of TXGAIN to amplifier 28 and then exits.

Figure 7A:
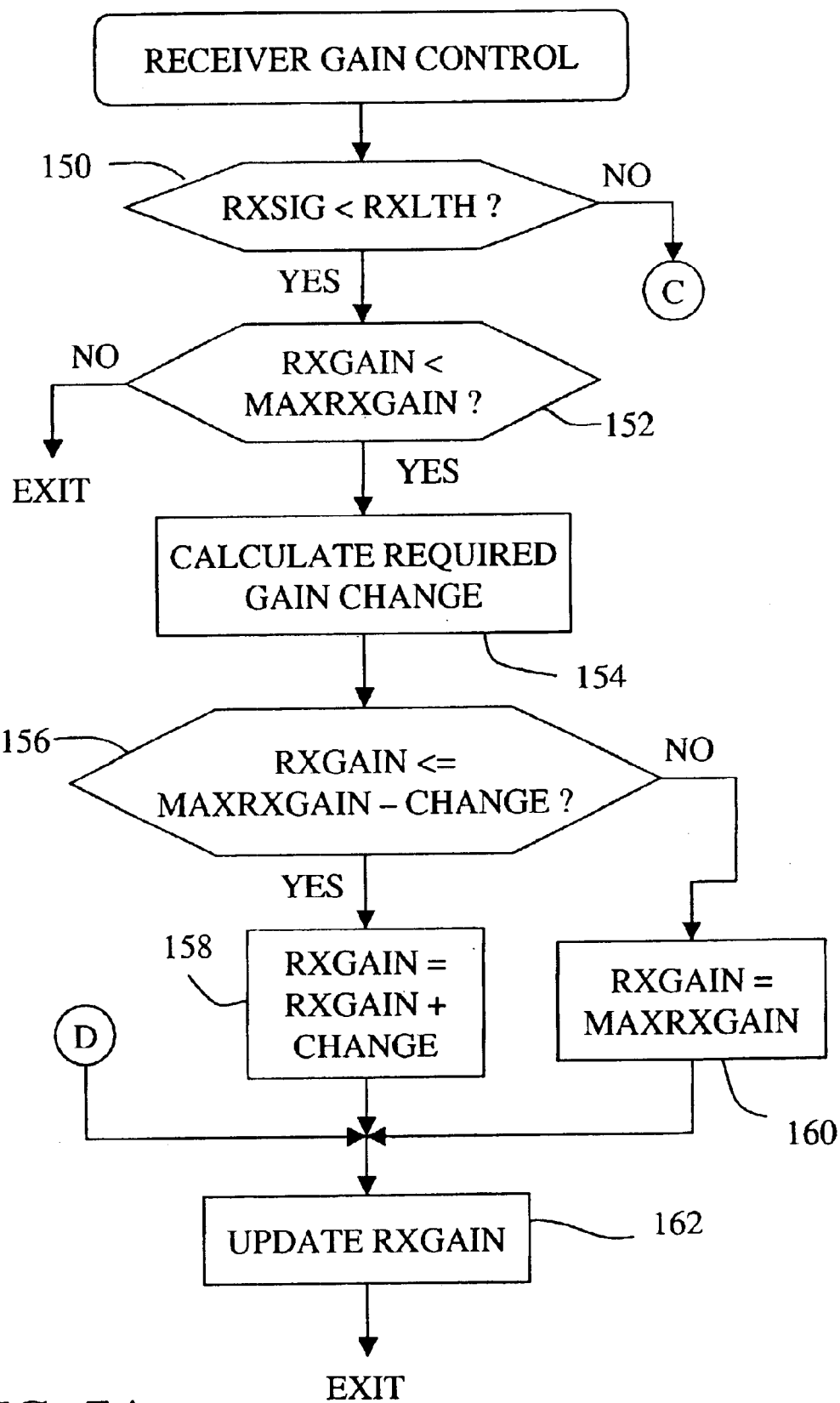
Figure 7B:
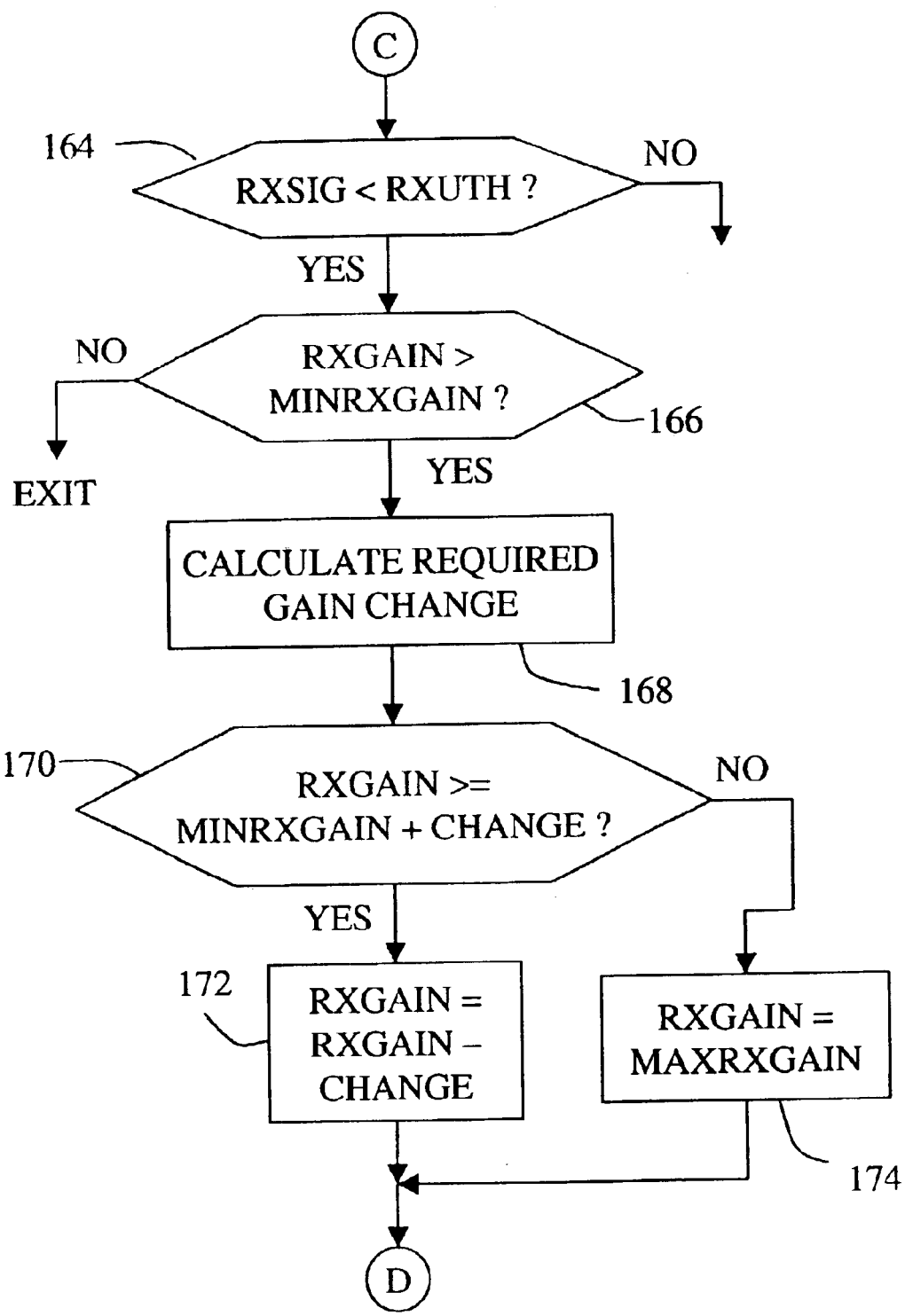

FIG. 7A-7B show a flow chart for the routine RECEIVER GAIN CONTROL. The routine begins at step 150 by determining if the demodulated and low pass filtered receiver signal RXSIG from filter 44 is less than a lower threshold RXLTH. If so, the routine determines at step 152 if the value of RXGAIN is less than a maximum MAXRX-GAIN. If the answer is no, the routine exits; but if the answer is yes the routine calculates a required gain change at step 154 as known in the art for the specific equipment used. From step 154, the routine proceeds to step 156, wherein it determines if the full gain change is allowed: that is, if gain RXGAIN is less than or equal to the maximum gain MAXRXGAIN minus the required change. If the answer is yes, the routine adds the required change to update receiver gain RXGAIN at step 158. If the answer is no, the routine alternatively limits the updated gain to MAXRXGAIN at step 160. From either of steps 158 and 160, the routine proceeds to step 162, wherein the updated receiver gain RXGAIN is output to amplifier 44 and the routine exits.

Returning to step 150, if the demodulated and low pass filtered receiver signal RXSIG from filter 44 is not less than the lower threshold RXLTH, the routine proceeds to step 164 in FIG. 7B, via tab C. The routine determines at step 164 if the value of RXSIG is greater than an upper threshold RXUTH. If not, the routine exits; but if so the routine determines at step 166 if RXGAIN is greater than a minimum MINRXGAIN. If the answer is no the routine exits; but with a yes answer, the routine calculates a required gain change at step 168 as known in the art for the specific equipment used. From step 168, the routine proceeds to step 170, wherein it determines if the full gain change is allowed: that is, if gain RXGAIN is greater than or equal to the minimum gain MINRXGAIN plus the required change. If the answer is yes, the routine subtracts the required change to update receiver gain RXGAIN at step 172. If the answer is no, the routine alternatively limits the updated gain to MINRXGAIN at step 174. From either of steps 172 and 174, the routine proceeds via tab D to step 162 in FIG. 7A, wherein the updated receiver gain RXGAIN is output to amplifier 44 and the routine exits.

Figure 8A:
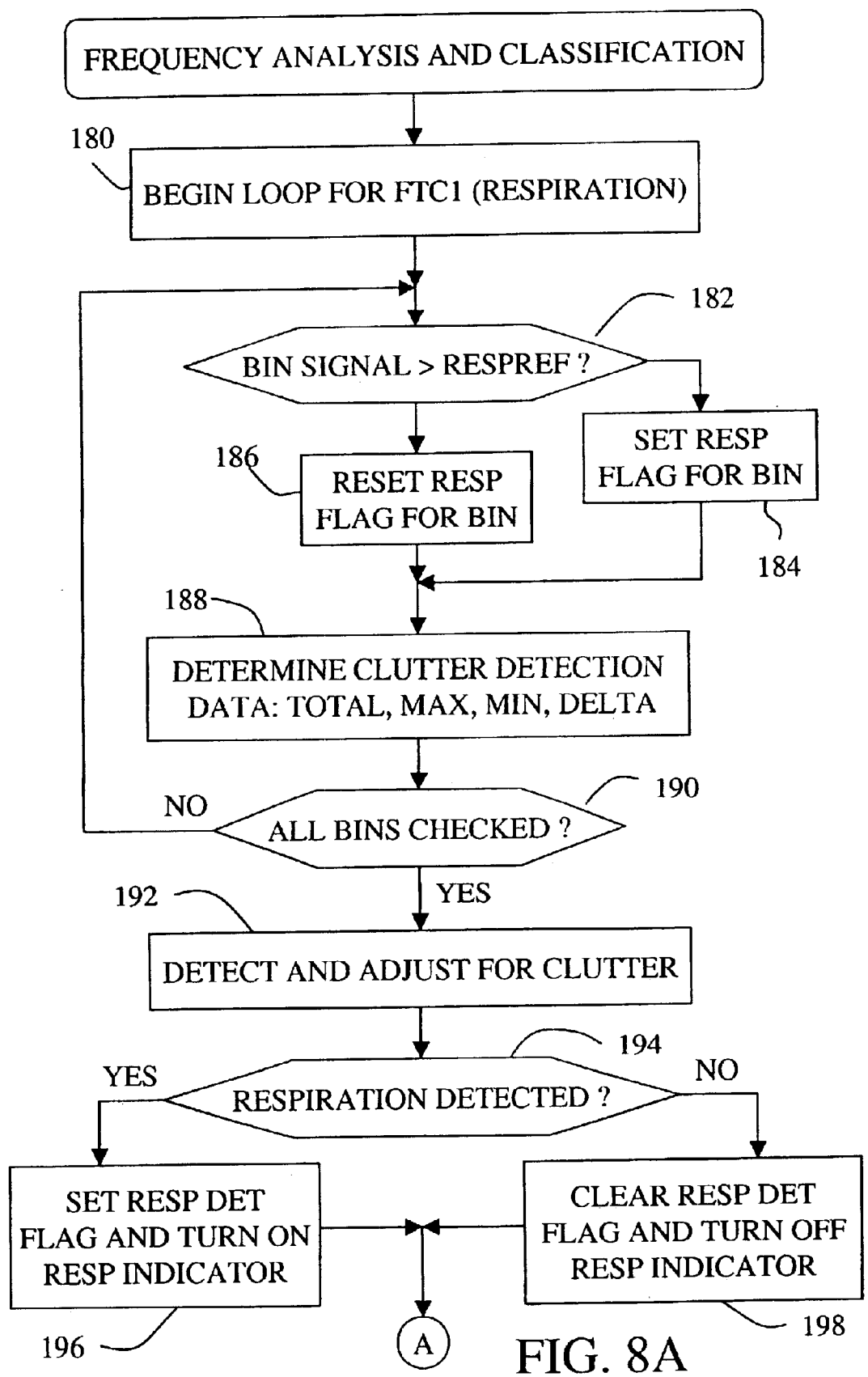
Figure 8B:
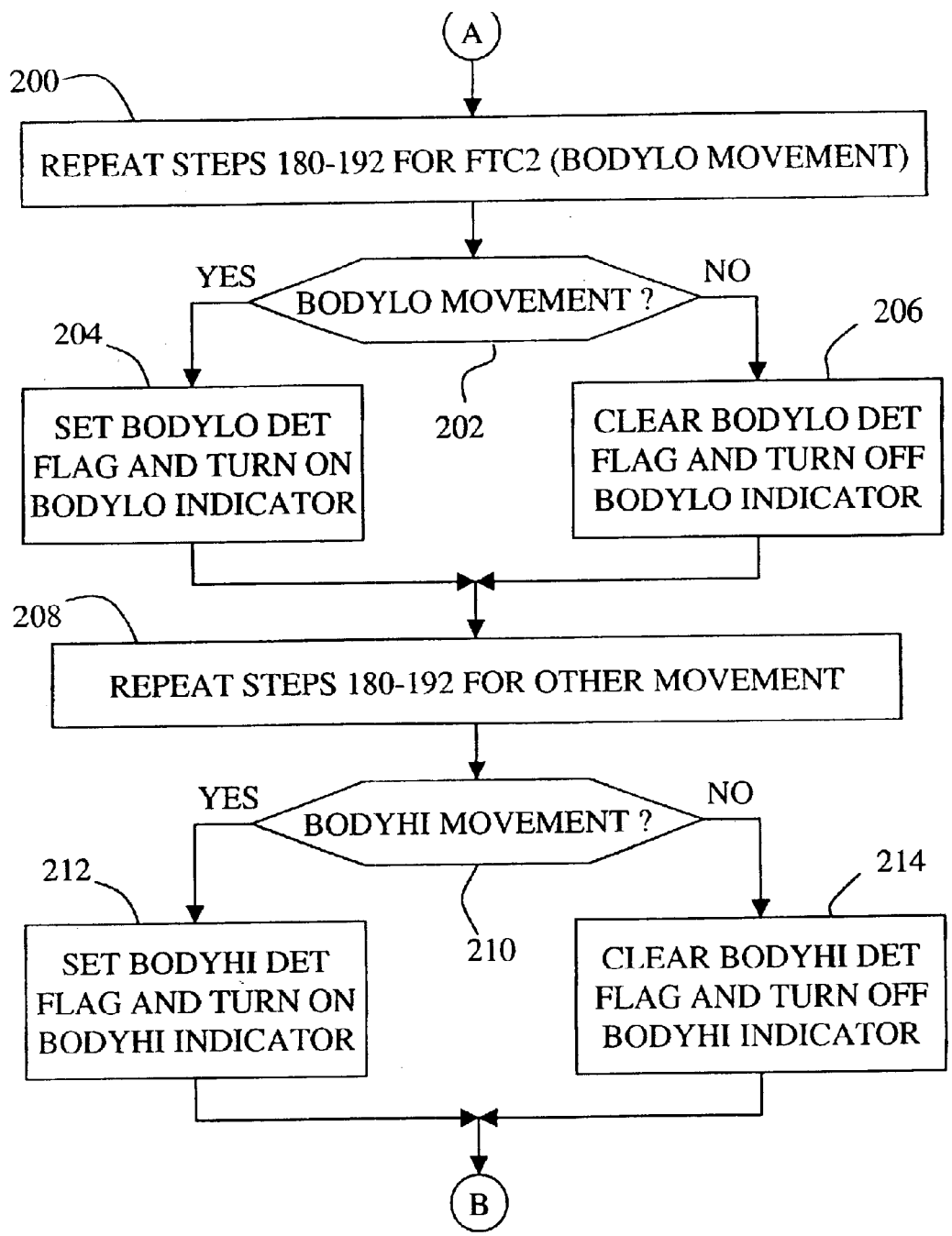
Figure 8C:
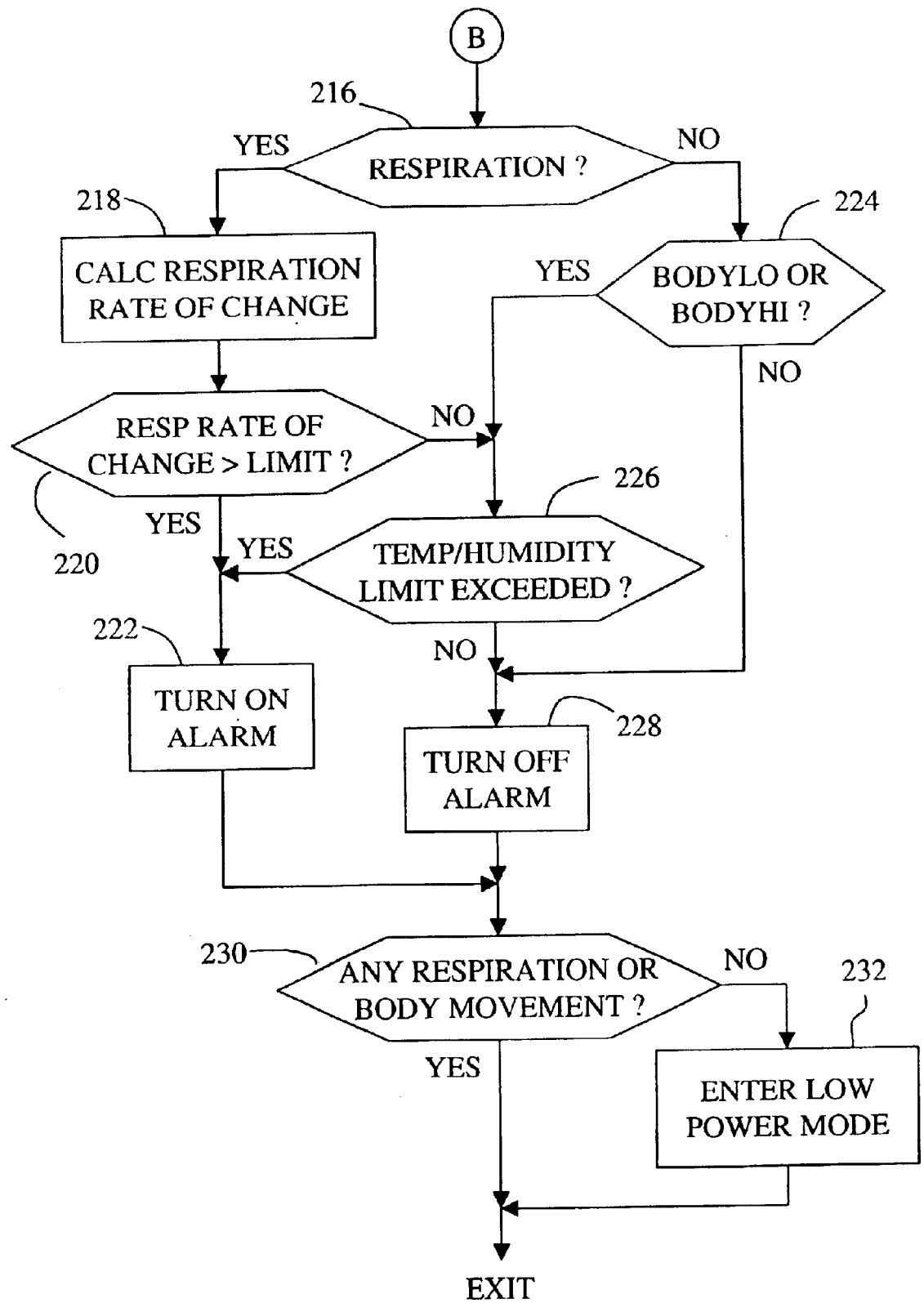

FIG. 8A-8C show a flow chart of routine FREQUENCY ANALYSIS AND CLASSIFICATION. At step 180 a frequency bin of the lower frequency band (FCT1) is selected to begin a loop. At step 182 the current, measured value of the filtered signal in the selected frequency bin X (BIN SIGNAL$_X$) is compared at step 182 with a predetermined, calibrated reference value RESPREF$_X$ and a flag RESP$_X$ is set at step 184 if the measured value exceeds the reference value and alternatively reset at step 186 if the measured value does not exceed the reference value. Stored reference values RESPREF$_X$ may be the same or different for the plurality of frequency bins, at the discretion of the system designer in view of system requirements. The setting of this flag is not a final decision that respiration is detected; such a decision may require a plurality of such findings consecutively or a predetermined number of findings within a predetermined number of determination attempts; and thus a recent, updated history of the value of the flag for each frequency bin and program loop is preferably maintained, for example as individual bits in stored variables that can be loaded into registers and tested.

From either of steps 184 and 186, the routine proceeds to step 188, in which certain clutter detection data for variable FCT1 is updated for the contribution from the selected frequency bin. Clutter is a phenomenon that may occur in some applications of this invention, wherein a motion disturbance from an external source, such as for example a cooling fan, provides additional interference in the acoustic medium of the detection volume or space that might produce false triggers and/or false occupant decisions under high gain settings. If clutter of this sort is present, the remedy is a forced gain reduction; and a clutter detection algorithm has proven useful in some testing to provide such gain reduction for more reliable system performance.

For the clutter detection algorithm, which will be described below with reference to step 192, an average value of the signal is calculated over a time interval of a predetermined number of program loops (e. g. 32). In addition, a Delta value (maximum–minimum) for the selected frequency bin is also calculated and stored. At step 188, which is within and is thus repeated for each individual frequency bin loop, certain data gathering and processing are performed to provide clutter detection variables from which the clutter may be determined at a later point. Specifically, the routine maintains values of the following clutter variables: (1) a total signal value RESP TOTAL, increased by summing the value of BIN SIGNAL for each consecutive frequency bin; (2) the maximum or peak value of BIN SIGNAL–RESP MAX—derived by comparing each consecutive value of BIN SIGNAL with a stored value of RESP MAX and replacing the latter with the former if it is greater in magnitude; (3) the minimum value of BIN SIGNAL–RESP MIN—derived by comparing each consecutive value of BIN SIGNAL with a stored value of RESP MIN and replacing the latter with the former if it is smaller in magnitude; and (4) RESP DELTA=RESPMAX–RESP MIN.

At step 190, the routine determines if all frequency bins have been checked for this program loop. If they have not, the routine returns to step 182 to repeat the loop for the next frequency bin. But if they have all been checked, the routine proceeds to step 192, wherein clutter determination and adjustment is performed.

The basic clutter detection algorithm operation is based on a philosophy that a range of frequency bins under normal operating conditions without disturbance or valid signals would have near zero values. Normally, a valid signal in one or more of these frequency bins will cause a Delta value greater than the average value of the data in the range of bins. However, "Clutter" conditions will yield Delta values lower than the average value as the various frequency bins (and associated filters) deal with random transients that are amplified by the higher gain settings. The data determined and stored in step 188 over the predetermined period provides a Delta value RESP DELTA, as well as an overall total value RESP TOTAL that can be divided conveniently by register shifting to provide an average value RESP AVG. Once this average is obtained, it is compared to lower and upper threshold values (in this case LTH=50 and UTH=75).

If the average value RESP AVG is between the LTH and UTH, and the Delta value RESP DELTA is below the average, the "Clutter" condition is considered to be present. The pseudo code is:

```
IF (LTH<=RESP AVG<=UTH AND RESP
   DELTA<RESP AVG)
   CLUTTER=TRUE;
ELSE
   CLUTTER=FALSE;
```

The appropriate response of the sensor under Clutter conditions is to reduce the receiver gain. Reducing the gain will reduce the sensitivity of the sensor and reduce the false occupant detection decisions under these conditions. When Clutter is not present, the normal closed loop control algorithm of the sensor controls the gain for the specific frequency band of the sensor. In applications of the invention wherein such clutter appears to be a problem, careful design of the filters and gain control apparatus may reduce clutter controlled gain reduction or even eliminate need for use of the clutter algorithm. It should further be noted that the detection of clutter and adjustment of receiver gain does not, in this embodiment, lead to a rejection of a finding of respiration or other body movement by the system.

At step 194, the determination is made whether respiration has been detected. This is preferably accomplished by testing the stored record of the respiration flag $RESP_F$ for each frequency bin F to determine whether the conditions for declaring respiration have been met. For example, if the requirement is that the respiration flag was set 5 consecutive times, or for 7 times out of 9, then a finding of such a record for any of the frequency bins causes a respiration flag RESP to be set at step 196 and a respiration indicator to be turned on. If the conditions have not been satisfied, then the respiration flag is cleared at step 198 and the respiration indicator turned off.

Continuing in FIG. 8B, at step 200 the process described in steps 180–192 is repeated, with such variations as are chosen, for any other frequency range useful for occupant classification, such as the portion of the 20–300 Hertz range of variable FCT2 characteristic of many other body movements of living beings having frequencies in the BODYLO range 2–20 Hertz (the lowest three frequency bins of TABLE 1). At step 202, a test similar to that of step 194 is performed for the chosen frequency range of body movement. If such movement is determined, a body movement flag BODYLO is set and a BODYLO movement indicator turned on at step 204. If not, the BODYLO movement flag is cleared and the indicator turned off at step 206. More specific frequency ranged may be similarly tested as desired. Finally, at step 208 the steps of 180–192 are performed for other detected movements, such as the portion of the 20–300 Hertz range of variable FCT2 characteristic of many other body movements of living beings having frequencies in the BODYHI range 20–300 Hertz (the highest seven frequency bins of TABLE 1). A test similar to that of step 194 is performed at step 210; and an other movement flag BODYHI is set and an other movement indicator is turned on at step 212 if such movement is determined. This flag is cleared and the BODYHI movement indicator is turned off if no such movement is detected.

Continuing in FIG. 8C, if the RESP flag is set at step 216, the respiration rate is determined at step 218. The basis of this determination is the frequency of the frequency bin F within the respiration band having a value above a predetermined reference. It is also possible to detect multiple respiring occupants if more than one such frequency bin exceeds the reference, particularly if those frequency bins are separated by a frequency bin with a lower signal value. Of course, any know data reduction technique such as statistical or other analyzes may be employed to optimize the determination. Next, at step 220, the rate of change of the respiration rate may be calculated (such as by the difference in consecutive respiration rates on a repeated computer cycle), and compared with a predetermined limit reference. It is contemplated that the absolute value of the change in respiration rate will be used, although the sign or direction of change may be used to assist classification of the occupant's changes in status. For example, an increasing rate of change may indicate stress; while a decreasing rate of change might indicate relaxation. The rate of change may additionally be combined with the respiration rate itself for further sophistication of the determination. If the result of the test at step 220 indicates a large change (particularly increasing) in the respiration rate, an alarm may be turned on at step 222.

If the respiration rate does not exceed the limit reference value at step 220, the routine proceeds to check the temperature and/or humidity level(s) at step 226. Elevated temperature and humidity are indicators of possible stress to a trapped occupant, even if the respiration rate has not increased greatly. If the level(s) are sufficiently high the routine will proceed to step 222 and turn on the alarm. If not, the routine turns off the alarm at step 228. Returning to step 224, if no respiration is detected the routine proceeds to step 224. If another body movement is detected (that is, if either of the BODYLO and BODYHI flags is set) at step 224, the routine proceeds to step 226 and follows the decision made at that step, described above. If both these flags are cleared, step 226 is skipped; and the routine turns off the alarm at step 228.

At step 230, all three flags (RESPIRATION, BODYLO, BODYHI) are checked. If any is set, the routine exits, leaving on any indicator of detected movement that was turned on in step 196, 204 or 212. If none is set, the system enters a low power mode at step 232 and exits, leaving all indicators off.

What is claimed is:

1. A method for classifying an occupant in a predetermined volume comprising:

transmitting an ultrasonic signal having a predetermined transmitter amplitude and a predetermined ultrasonic frequency through the predetermined volume;

receiving a composite ultrasonic signal comprising a signal component produced by interference between the transmitted ultrasonic signal and a returning reflection of the transmitted ultrasonic signal from an occupant within the predetermined volume;

amplitude demodulating the composite ultrasonic signal to isolate the signal component;

analyzing the signal component to derive frequency data therefrom; and classifying the occupant within the predetermined volume from the derived frequency data of the interference signal component.

2. The method of claim 1 wherein the step of classifying the occupant further comprises the steps:

storing frequency data characteristic of a live occupant movement;

comparing the derived frequency data with the stored frequency data; and classifying the occupant as a living being if the derived frequency data and the stored frequency data match within predetermined criteria.

3. The method of claim 2 wherein:
the stored frequency data defines a reference value in a frequency range characteristic of respiration;
the step of analyzing the signal component further comprises deriving from the signal component a measured value within the frequency range characteristic of respiration; and
the step of comparing the derived frequency data further comprises comparing the measured value in the frequency range of respiration with the reference value in the frequency content in the frequency range of respiration.

4. The method of claim 2 wherein:
the stored frequency data defines reference values in a plurality of frequency sub-ranges within a frequency range of respiration;
the step of analyzing the signal component further comprises deriving from the signal component a measured frequency value within at least one of the frequency sub-ranges;
the step of comparing the derived frequency data further comprises comparing the measured value in the one of the frequency sub-ranges with the reference value in the one of the frequency sub-ranges.

5. The method of claim 2 wherein:
the stored frequency data defines reference values in a plurality of frequency sub-ranges within a frequency range of respiration;
the step of analyzing the signal component further comprises determining a measured frequency value within each of the frequency sub-ranges;
the step of comparing the derived frequency data with the stored frequency data comprises comparing the measured value and the reference value in each of the frequency sub-ranges; and
the occupant is classified as a living being if the measured value at least equals the reference value in at least one of the frequency sub-ranges.

6. The method of claim 5 wherein, if the measured value at least equals the reference content in the one of the frequency sub-ranges, a frequency of respiration associated with the one of the frequency sub ranges is determined.

7. The method of claim 6 wherein the steps of claim 6 are repeated after a predetermined time; and, if a first frequency of respiration is determined in the steps of claim 6 and a second frequency of respiration is similarly determined in the repetition of the steps of claim 6:
a change in respiration rate is derived from a difference between the first frequency of respiration and the second frequency of respiration; and
the occupant is further classified on the basis of the rate of change of respiration represented.

8. The method of claim 1 wherein the step of transmitting an ultrasonic signal further comprises the step of controlling the amplitude of the transmitted ultrasonic signal in response to a voltage level of electric power supplied to the transmitter.

9. The method of claim 1 wherein the step of receiving an ultrasonic signal further comprises the step of amplifying the received composite signal with a gain controlled amplifier in an automatic gain control loop.

10. The method of claim 9 wherein step of transmitting an ultrasonic signal further comprises reducing the amplitude of the transmitted ultrasonic signal when a gain of the gain controlled amplifier in the automatic gain control loop used in receiving an ultrasonic signal is no greater than a minimum desired value.

11. Apparatus for classifying an occupant in a predetermined volume comprising:
means for transmitting an ultrasonic signal having a predetermined transmitter amplitude and a predetermined ultrasonic frequency through the predetermined volume;
means for receiving a composite ultrasonic signal comprising a signal component produced by interference between the transmitted ultrasonic signal and a returning reflection of the transmitted ultrasonic signal from an occupant within the predetermined volume;
means for amplitude demodulating the composite ultrasonic signal to isolate the signal component;
means for analyzing the signal component to derive frequency data therefrom; and
means for classifying the occupant within the predetermined volume responsive to the derived frequency data of the interference signal component.

12. The apparatus of claim 11 wherein the means for classifying the occupant further comprises:
means for storing frequency data characteristic of a live occupant movement;
means for comparing the derived frequency data with the stored frequency data; and
means for classifying the occupant as a living being if the derived frequency data and the stored frequency data match within predetermined criteria.

13. The apparatus of claim 12 wherein:
the stored frequency data defines a reference value in a frequency range characteristic of respiration;
the means for analyzing the signal component further comprises means for deriving from the signal component a measured value within the frequency range characteristic of respiration; and
the means for of comparing the derived frequency data further comprises means for comparing the measured value in the frequency range of respiration with the reference value in the frequency content in the frequency range of respiration.

14. The apparatus of claim 12 wherein:
the stored frequency data defines reference values in a plurality of frequency sub-ranges within a frequency range of respiration;
the means for analyzing the signal component further comprises means for deriving from the signal component a measured frequency value within at least one of the frequency sub-ranges;
the means for comparing the derived frequency data further comprises means for comparing the measured value in the one of the frequency sub-ranges with the reference value in the one of the frequency sub-ranges.

15. The apparatus of claim 12 wherein:
the stored frequency data defines reference values in a plurality of frequency sub-ranges within a frequency range of respiration;
the means for analyzing the signal component further comprises means for determining a measured frequency value within each of the frequency sub-ranges;
the means for comparing the derived frequency data with the stored frequency data further comprises means for comparing the measured value and the reference value in each of the frequency sub-ranges; and the means for classifying an occupant further comprises means for classifying the occupant as a living being if the measured value at least equals the reference value in at least one of the frequency sub-ranges.

16. The apparatus of claim 12 wherein:

the stored frequency data defines reference values in a plurality of frequency sub-ranges within a frequency range of respiration;

the means for analyzing the signal component further comprises means for determining a measured frequency value within each of the frequency sub-ranges;

the means for comparing the derived frequency data with the stored frequency data further comprises means for comparing the measured value and the reference value in each of the frequency sub-ranges; and the means for classifying an occupant further comprises means for classifying the occupant as a living being having a frequency of respiration associated with the one of the frequency sub ranges if the measured value at least equals the reference value in at least one of the frequency sub-ranges.

17. The apparatus of claim 12 wherein:

the stored frequency data defines reference values in a plurality of frequency sub-ranges within a frequency range of respiration;

the means for analyzing the signal component further comprises means for repeatedly determining a measured frequency value within each of the frequency sub-ranges;

the means for repeatedly comparing the derived frequency data with the stored frequency data further comprises means for comparing the measured value and the reference value in each of the frequency sub-ranges; and the means for classifying and occupant further comprises means for deriving a rate of change of respiration from a difference frequency between frequency sub-ranges in which the measured value at least equals the reference value in at least two separate repeated comparisons.

18. The apparatus of claim 11 wherein the means for transmitting an ultrasonic signal further comprises means for controlling the amplitude of the transmitted ultrasonic signal in response to a voltage level of electric power supplied to the transmitter.

19. The apparatus of claim 11 wherein the means for receiving an ultrasonic signal further comprises means for amplifying the received composite signal with a gain controlled amplifier in an automatic gain control loop.

20. The apparatus of claim 19 wherein means for transmitting an ultrasonic signal further comprises means for reducing the amplitude of the transmitted ultrasonic signal when a gain of the gain controlled amplifier in the automatic gain control loop used in receiving an ultrasonic signal is no greater than a minimum desired value.

* * * * *